US008823515B2

(12) United States Patent
Rettedal et al.

(10) Patent No.: US 8,823,515 B2
(45) Date of Patent: Sep. 2, 2014

(54) COMPUTER IMPLEMENTED ANIMAL MANAGEMENT SYSTEM

(75) Inventors: Nicholas P. Rettedal, Fort Collins, CO (US); Stephen M. Weilnau, Greeley, CO (US); Scott R. Cockroft, Greeley, CO (US); Billy J. Yeager, Gilbert, AZ (US)

(73) Assignee: Bella Technologies, LLC, Kersey, CO (US)

( * ) Notice: Subject to any disclaimer, the term of this patent is extended or adjusted under 35 U.S.C. 154(b) by 82 days.

(21) Appl. No.: 13/391,614

(22) PCT Filed: Sep. 14, 2010

(86) PCT No.: PCT/US2010/002509
§ 371 (c)(1),
(2), (4) Date: Feb. 21, 2012

(87) PCT Pub. No.: WO2011/034577
PCT Pub. Date: Mar. 24, 2011

(65) Prior Publication Data
US 2012/0161964 A1    Jun. 28, 2012

Related U.S. Application Data

(60) Provisional application No. 61/276,723, filed on Sep. 15, 2009.

(51) Int. Cl.
*G08B 1/08* (2006.01)
*A01K 11/00* (2006.01)

(52) U.S. Cl.
CPC ............. *A01K 11/008* (2013.01); *A01K 11/006* (2013.01)
USPC .................................. 340/539.13; 340/572.1

(58) Field of Classification Search
USPC .................. 340/539.13, 539.12, 572.1, 10.1; 119/51.02
See application file for complete search history.

(56) References Cited

U.S. PATENT DOCUMENTS

| 5,818,354 | A | 10/1998 | Gentry |
| 5,963,132 | A * | 10/1999 | Yoakum ..................... 340/572.1 |
| 5,984,875 | A | 11/1999 | Brune |
| 6,099,482 | A | 8/2000 | Brune et al. |
| 6,371,927 | B1 | 4/2002 | Brune et al. |
| 7,962,096 | B2 * | 6/2011 | Cox ......................... 340/539.32 |
| 8,545,436 | B2 | 10/2013 | Robertson et al. |
| 8,547,248 | B2 | 10/2013 | Zdeblich et al. |
| 8,588,887 | B2 | 11/2013 | Arneson et al. |
| 2005/0134452 | A1 | 6/2005 | Smith |
| 2005/0145187 | A1 * | 7/2005 | Gray ........................... 340/10.1 |
| 2006/0185605 | A1 | 8/2006 | Renz et al. |
| 2007/0271320 | A1 | 11/2007 | Tsuyuzaki |

(Continued)

OTHER PUBLICATIONS

International PCT Patent Application No. PCT/US2010/002509, filed Sep. 14, 2010.

(Continued)

*Primary Examiner* — John A Tweel, Jr.
(74) *Attorney, Agent, or Firm* — Craig Miles; CR Miles, P.C.

(57) ABSTRACT

Specifically, a computer implemented animal management program having modules which function to match animal information retrieved from a radiofrequency identification device(s) implanted in an animal(s) with animal information retrieved from a database of at least one computer to assess animal condition and time treatment events.

25 Claims, 13 Drawing Sheets

(56) References Cited

U.S. PATENT DOCUMENTS

| | | |
|---|---|---|
| 2008/0104209 A1 | 5/2008 | Singhal et al. |
| 2008/0236500 A1 | 10/2008 | Hodges et al. |
| 2011/0212782 A1 | 9/2011 | Thompson et al. |
| 2012/0068848 A1 | 3/2012 | Campbell et al. |
| 2013/0231188 A1 | 9/2013 | Berberich et al. |

OTHER PUBLICATIONS

U.S. Appl. No. 61/276,723, filed Sep. 15, 2009.

Boehmer, et al. Effects of Temperature of Consumed Water on Rumen Temperature of Beef Cows. Oklahoma Agricultural Experiment Station, 2009, 4 total pages.

Cooper-Prado, et al. Relationship of Ruminal Temperature with Parturition and Estrus of Beef Cows. J Anim Sci, Apr. 2011, 89:1020-1027; published ahead of print Dec. 17, 2011.

Smartstock USA. Website, http://www.smartstock-usa.com, originally downloaded Dec. 30, 2011, 12 total pages.

Hach. Digital Inductive Conductivity Sensor, Convertible Body Style. Website, http:/www.hach.com, product page downloaded Mar. 5, 2014, 2 total pages.

Corresponding New Zealand patent application No. 599357; OA dated Oct. 19, 2012, 1 page.

Corresponding New Zealand patent application No. 599357; OA dated Feb. 8, 2013, 1 page.

Corresponding New Zealand patent application No. 599357; Letters Patent dated Sep. 3, 2012, 1 page.

New Zealand patent application No. 610343; OA dated Nov. 11, 2013, 3 total pages.

International Patent Cooperation Treaty Patent Application No. PCT/US2011/001788, filed Oct. 19, 2011.

U.S. Appl. No. 61/455,419, filed Oct. 19, 2010.

U.S. Appl. No. 13/824,270, filed Mar. 15, 2013.

\* cited by examiner

COMPUTER IMPLEMENTED ANIMAL MANAGEMENT SYSTEM

This application is the United States National Stage of International Patent Corporation Treaty Patent Application No. PCT/US2010/002509, filed Sep. 14, 2010, which claims the benefit of U.S. Provisional Patent Application No. 61/276,723, filed Sep. 15, 2009, each hereby incorporated by reference herein.

I. TECHNICAL FIELD

Generally, a computer implemented animal management system. Specifically, a computer implemented animal management method which matches animal information retrieved from a radiofrequency identification device implanted in an animal with animal information retrieved from a database of at least one computer.

II. BACKGROUND

A conventional radiofrequency identification device ("RFID" or "RFID device") is an object that can be attached to or incorporated into a product, animal, or person typically for the purpose of locating and identification of that object using radio waves. Certain RFID devices can be written to and read from a distance away and do not have to be in the line of sight of a RFID device writer or reader. The current thrust in RFID device use is in supply chain management for large enterprises. RFID devices increase the speed and accuracy with which inventory can be tracked and managed thereby saving money for the business.

Conventional RFID devices (such as tags, labels, dots or the like) contain at least two parts. One is an integrated circuit for storing and processing information, modulating and demodulating a radio frequency (RF) signal and perhaps other specialized functions. The second is an antenna for receiving and transmitting the radio signal. A technology called chipless RFID allows for discrete identification of RFID devices without an integrated circuit, thereby allowing tags to be printed directly onto assets at lower cost than traditional RFID. For example, in 2006, Hitachi, Ltd. developed a passive device called the µ-Chip measuring 0.15×0.15 mm (not including the antenna), and thinner than a sheet of paper (about 7.5 micrometers) silicon-on-Insulator (SOI) technology is used to achieve this level of integration. The Hitachi µ-Chip can wirelessly transmit a 128-bit unique identification number which is hard coded into the chip as part of the manufacturing process. The unique ID in the chip cannot be altered, providing a high level of authenticity to the chip and ultimately to the items the chip may be permanently attached or embedded into. The Hitachi µ-Chip has a typical maximum read range of 30 cm (1 foot). In February 2007, Hitachi unveiled an even smaller RFID device measuring 0.05×0.05 mm, and thin enough to be embedded in a sheet of paper.

An RFID device interrogator, also referred to as a RFID reader, is an electronic device that receives the radio signal from the RFID device. In many cases, the interrogator also generates the interrogation signal. Interrogators or readers require a power supply, network connection, and antenna in order to function. Depending on application, these components may be separate or integrated. Interrogators come in various constructional forms and methods of operation.

A significant problem with RFID devices can be that the memory in which data can be stored is limited. As a non-limiting example, the 128 bit ROM above-described can only store one unique 38 digit identification number. Understandably, as the number of bits which can be encoded on a RFID increases so does the cost and the size of the RFID. Accordingly, the ROM of RFID devices utilized for tracking, locating and identification of goods remains between 100 and 200 bits and certain ROM of RFID devices include even fewer bits such as 50-100 bits ROM, or even fewer bits.

Another significant problem with RFID devices may be that there is no computer implemented animal management system available for encoding and updating RFID information of an RFID implanted in an animal and integrating the RFID information with relational and storage databases in a server or remote computer for the purpose of remotely monitoring, tracking, sorting, diagnosing, or treating each RFID implanted animal.

The inventive computer implemented animal management system described herein addresses each of these problems by providing computer implemented functions which provide a method which matches animal information retrieved from a radiofrequency identification device implanted in an animal to animal information retrieved from a database of at least one computer.

III. DISCLOSURE OF INVENTION

Accordingly, a broad object of the invention is to provide an inventive RFID implantable in an RFID object such as an animal or other asset and a RFID reader which can retrieve RFID information from the implanted RFID and computer implemented animal management program (also referred to as an animal management application) which provides executable program instructions in the form of various program modules each of which function to integrate retrieved RFID data with data in relational database tables and storage database tables or analyze the RFID data and data from relational databases for each RFID implanted in an animal.

A second broad object of the invention can be to provide computer implemented instructions of an animal management program which in part automatically enters retrieved RFID information into relational database tables and storage database tables for each RFID implanted in an animal and further provides a manual data entry module which upon activation allows animal information to be manually entered into relational database tables and storage database tables for each RFID implanted in an animal.

A third broad object of the invention can be to provide computer implemented instructions of an animal management program which in part provides an alert module which generates lists of animals implanted with RFID having sensor which provides sensed animal information which falls outside of pre-established threshold values for a particular sensed animal characteristic or sensed incorrect animal location.

A fourth broad object of the invention can be to provide computer implemented instructions for entry and monitoring diagnosis and treatment plans for animal having sensed animal information which falls outside of pre-established threshold values for a particular sensed animal characteristic.

A fifth broad object of the invention can be to provide computer implemented instructions for automatically sorting animals implanted with RFID based on sensed animal information and animal information in relational database tables and storage database tables into groups that can be optimally located together.

Naturally, further objects of the invention are disclosed throughout other areas of the specification, drawings, photographs, and claims.

IV. BRIEF DESCRIPTION OF THE DRAWINGS

V. MODE(S) FOR CARRYING OUT THE INVENTION

Figure 1:
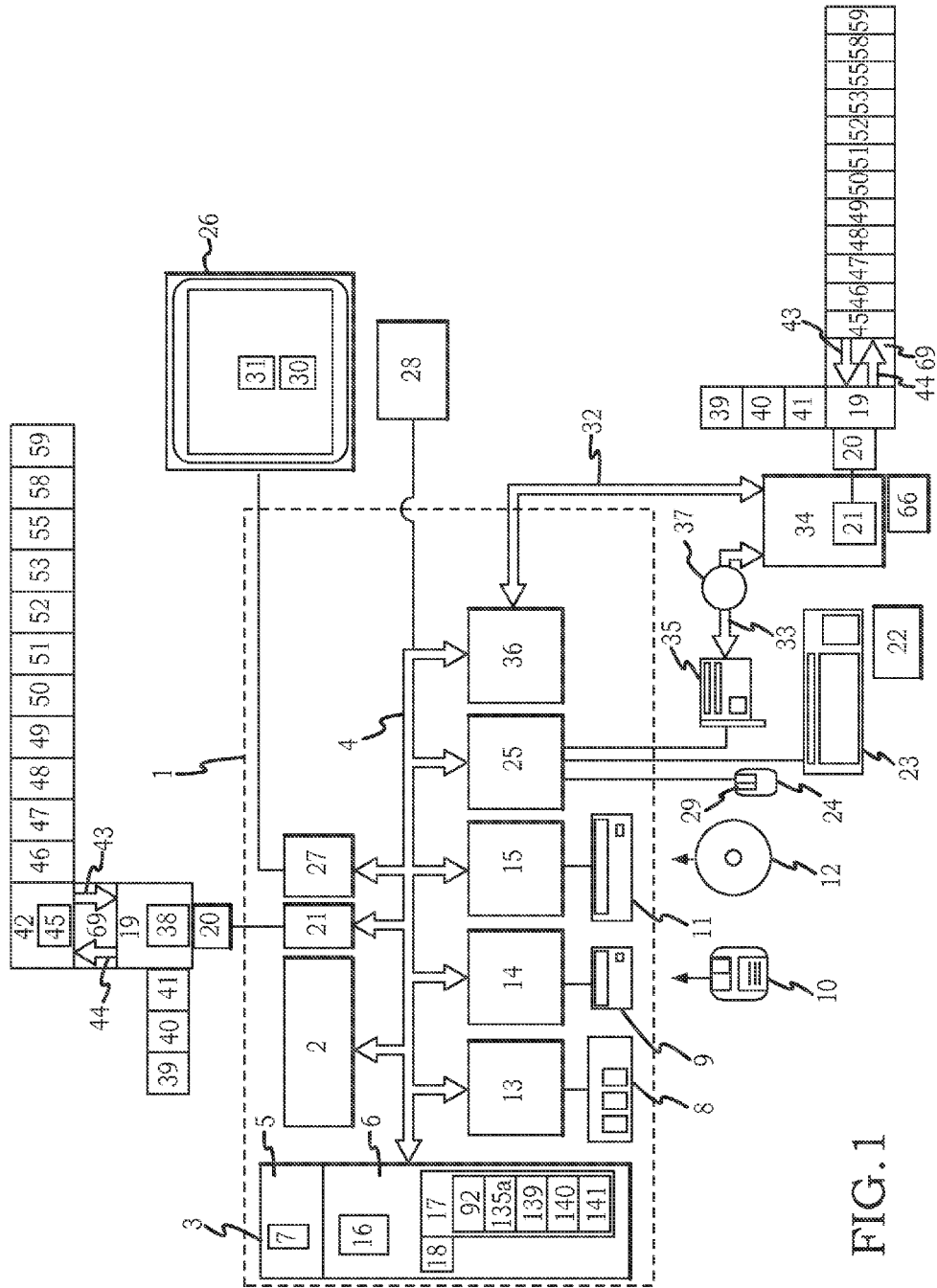
FIG. 1 is a block diagram of particular computer means and radiofrequency identification means of a particular embodiment of the invention.

Generally, a computer implemented animal management system. Specifically, a computer implemented animal management program having modules which function to match animal information retrieved from a radiofrequency identification device(s) implanted in an animal(s) with animal information retrieved from a database of at least one computer to assess animal condition and time treatment events.

The inventive computer implemented animal management system may be described herein in terms of functional block components, screen shots, and various process steps. It should be appreciated that such functional blocks may be realized by any number of hardware or software components configured to perform the specified functions. For example, the inventive computer implemented animal management system may employ various integrated circuit components which function without limitation as memory elements, to modulate and demodulate radio frequency signal, processing elements, logic elements, look-up tables, or the like, which may carry out a variety of functions under the control of one or more microprocessors or other control devices.

Similarly, the software elements of the present invention may be implemented with any programming or scripting language such as C, C++, Java, COBOL, assembler, PERL, Labview or any graphical user interface programming language, extensible markup language (XML), Microsoft's Visual Studio .NET, Visual Basic, or the like, with the various algorithms or Boolean Logic being implemented with any combination of data structures, objects, processes, routines or other programming elements. Further, it should be noted that the present invention might employ any number of conventional wired or wireless techniques for data transmission, signaling, data processing, network control, and the like.

It should be appreciated that the particular implementations shown and described herein are illustrative of the invention and its best mode and are not intended to otherwise limit the scope of the present invention in any way. Indeed, for the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical data encoding-decoding system.

As will be appreciated by one of ordinary skill in the art, the present invention may be embodied as a method, a data processing system, a device for data processing, a computer program product, or the like. Accordingly, the present invention may take the form of an entirely software embodiment, an entirely hardware embodiment, or an embodiment combining aspects of both software and hardware. Furthermore, the present invention may take the form of a computer program product on a computer-readable storage medium having computer-readable program code means embodied in the storage medium. Any suitable computer-readable storage medium may be utilized, including, but not limited to hard disks, CD-ROM, optical storage devices, magnetic storage devices, ROM, flash RAM, or the like.

The present invention may be described herein with reference to screen shots, block diagrams and flowchart illustrations of the animal management system to describe computer programs, applications, or modules which can be utilized separately or in combination in accordance with various embodiments or functions of the invention. It will be understood that each functional block of the block diagrams and the flowchart illustrations, and combinations of functional blocks in the block diagrams and flowchart illustrations, respectively, can be implemented by computer program instructions. These computer program instructions may be loaded onto a general purpose computer, special purpose computer or other programmable data processing apparatus to produce a machine, such that the instructions which execute on the computer or other programmable data processing apparatus for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of components for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware based computer systems which perform the specified functions or steps, or suitable combinations of special purpose hardware and computer instructions.

Now referring primarily to FIG. 1, which shows a block diagram of a non-limiting embodiment of a computer and related elements which can be utilized to implement embodiments of a computer implemented animal management system including, without limitation, a server computer (1) having at least one processing unit (2), a memory element (3), and a bus (4) which operably couples components of the server computer (1), including, without limitation the memory element (3) to the processing unit (2). The server computer (1) may be a conventional computer, a distributed computer, or any other type of computer which may contain all or a part of the elements described or shown to accomplish the functions described herein; the invention is not so limited. The processing unit (2) can comprise without limitation one central-processing unit (CPU), or a plurality of processing units which operate in parallel to process digital information, or a digital signal processor (DSP) plus a host processor, or the like. The bus (4) can be without limitation any of several types of bus configurations such as a memory bus or memory controller, a peripheral bus, and a local bus using any of a variety of bus architectures. The memory element (3) can without limitation be a read only memory (ROM) (5) or a random access memory (RAM) (6), or both. A basic input/output system (BIOS) (7), containing routines that assist transfer of data between the components of the server computer (1), for example during start-up, can be stored in ROM (5). The computer (1) can further include a hard disk drive (8) for reading from and writing to a hard disk (not shown) a magnetic disk drive (9) for reading from or writing to a removable magnetic disk (10), and an optical disk drive (11) for reading from or writing to a removable optical disk (12) such as a CD ROM or other optical media.

The hard disk drive (8), magnetic disk drive (9), and optical disk drive (10) can be connected to the bus (4) by a hard disk drive interface (13), a magnetic disk drive interface (14), and an optical disk drive interface (15), respectively. The drives and their associated computer-readable media provide non-volatile storage of computer-readable instructions, data structures, program modules and other data for the server computer (1). It can be appreciated by those skilled in the art that any type of computer-readable media that can store data that is accessible by a computer, such as magnetic cassettes, flash memory cards, digital video disks, Bernoulli cartridges, random access memories (RAMs), read only memories (ROMs), RFID devices or the like, may be used in the exemplary operating environment.

The server computer (1) can further include an operating system (16) and an inventive animal management application (17) which as to certain embodiments of the invention can include a radiofrequency identification ("RFID") encoder-decoder application (18) which functions to encode and decode RFID data (38) to and from a RFID device (19) (the RFID device typically comprising a programmable microcircuit and an antenna which can be affixed to a wide variety of materials in numerous and varied constructional forms) using a RFID programmer (20) connected to the bus (4) by a RFID interface (21) may be stored on or in the hard disk, magnetic disk (10), optical disk (12), ROM (5), in RAM (6) as shown by the particular embodiment of a server computer (1) shown in FIG. 1, or alternately the functionalities of the data encoder-decoder application (18) may be implemented as an application specific integrated chip (ASIC) or file programmable gate array (FPGA), or the like.

A computer user (22) can enter commands and information into the server computer (1) through input devices such as a keyboard (23) and a pointing device (24) such as a mouse. Other input devices (not shown) may include a microphone, joystick, game pad, satellite dish, scanner, magnetic strip of a card, or the like. These and other input devices are often connected to the processing unit (2) through a serial port interface (25) that can be coupled to the bus (4), but may be connected by other interfaces, such as a parallel port, game port, or a universal serial bus (USB). A monitor (26) or other type of display device can also be connected to the bus (4) via interfaces such as a video adapter (27), or the like. In addition to the monitor (26), the server computer (1) can further include a peripheral output device(s) (28), such as speakers and printers.

A "click event" occurs when the computer user (22) operates at least one function of the animal management application (17) or the RFID device encoder-decoder application (18), or other program or other application function, through an action or the use of a command which for example can include pressing or releasing a left mouse button (29) while a pointer element (30) is located over a control icon (31) displayed on the monitor (26). However, it is not intended that a "click event" be limited to the press and release of the left button (29) on a mouse (24) while a pointer element (30) is located over a control icon (31). Rather, the term "click event" is intend to broadly encompass any action or command by the computer user (22) through which a function of the operating system (16) or the animal management application (17), or the RFID device encoder-decoder application (18), or other program or application is activated or performed, whether through clickable selection of one or a plurality of control icon(s) (31) or by computer user (22) voice command, keyboard stroke(s), mouse button, touch screen, touch pad, or otherwise. It is further intended that control icons (31) can be configured without limitation as a point, a circle, a triangle, a square (or other geometric configurations or combinations or permutations thereof), or as a check box, a drop down list, a menu, or other index containing a plurality of selectable options, an information field which can contain or which allows input of a string of alphanumeric characters such as a street address, zip code, county code, or natural area code, animal identification number or by inputting a latitude/longitude or projected coordinate X and Y, animal pen number, or other notation, script, character, or the like.

The server computer (1) may operate in a networked environment using logical connections (32)(33) to one or a plurality of remote computers (34). These logical connections (32)(33) are achieved by a communication device (35)(36) coupled to or a part of the server computer (1). Each of the plurality of remote computers (34) can include a part or all of the elements above-described as included in the server computer (1) although only a single box has been illustrated in FIG. 1 for the remote server computer (34). The logical connections (32)(33) depicted in FIG. 1 can establish a local-area network (LAN) or a wide-area network (WAN). Such networking environments are commonplace in offices, enterprise-wide computer networks, intranets and the Internet (37).

When used in a LAN-networking environment, the server computer (1) can be connected to the local network through a network interface (36) type of communications device. When used in a WAN-networking environment, the server computer (1) typically includes a modem (35), a type of communications device, or any other type of communications device for establishing communications over the WAN, such as the Internet (64). The modem (35), which may be internal or external, is connected to the bus (4) via the serial port interface (25). In a networked environment, the data encoder-decoder application (17), or portions thereof, may be stored in any one or more of the plurality of remote computers (34). It is appreciated that the logical connections (32)(33) shown are exemplary and other hardware means and communications means can be utilized for establishing a communications link between the server computer (1) and one or more of the a plurality of remote computers (35).

While the computer means and the network means shown in FIG. 1 can be utilized to practice the invention including the best mode, it is not intended that the description of the best mode of the invention or any preferred embodiment of the invention be limiting with respect to the utilization of a wide variety of similar, different, or equivalent computer means or network means to practice embodiments of the invention which include without limitation hand-held devices, such as personal digital assistants or camera/cell phone, multiprocessor systems, microprocessor-based or programmable consumer electronics, network PCs, minicomputers, mainframe computers, PLCs, or the like.

With respect to those embodiments of the invention which provide the RFID encoder-decoder application (18), the animal tracking system can further include a RFID interface (21) and a RFID programmer (20) for programming RFID data (38) to a RFID (19). The term RFID (19) for the purposes of this invention can be any type of radiofrequency identification device as above-above described or otherwise which can be attached, incorporated, implanted, imprinted, or held (individually and collectively referred to herein as "implanted") on or within an RFID object (39). For the purposes of this invention, an RFID object (39) can include any manner of object to which an RFID (19) can be implanted and while examples of particular embodiments of the invention are described in the context of an animal tracking system, an animal management system, or attaching, applying, implanting or otherwise coupling an RFID (19) to an animal (40) (or a plurality of animals) such as cattle, deer, sheep, pigs, or the like, the invention is not so limited and the functionalities described herein can be applied in general to asset tracking systems, asset management system in which an RFID can be attached, applied, implanted or otherwise coupled to an asset (41) such as goods whether being transported or in inventory, packages, component parts whether in a manufacturing process or during transit, or the like.

Figure 2:
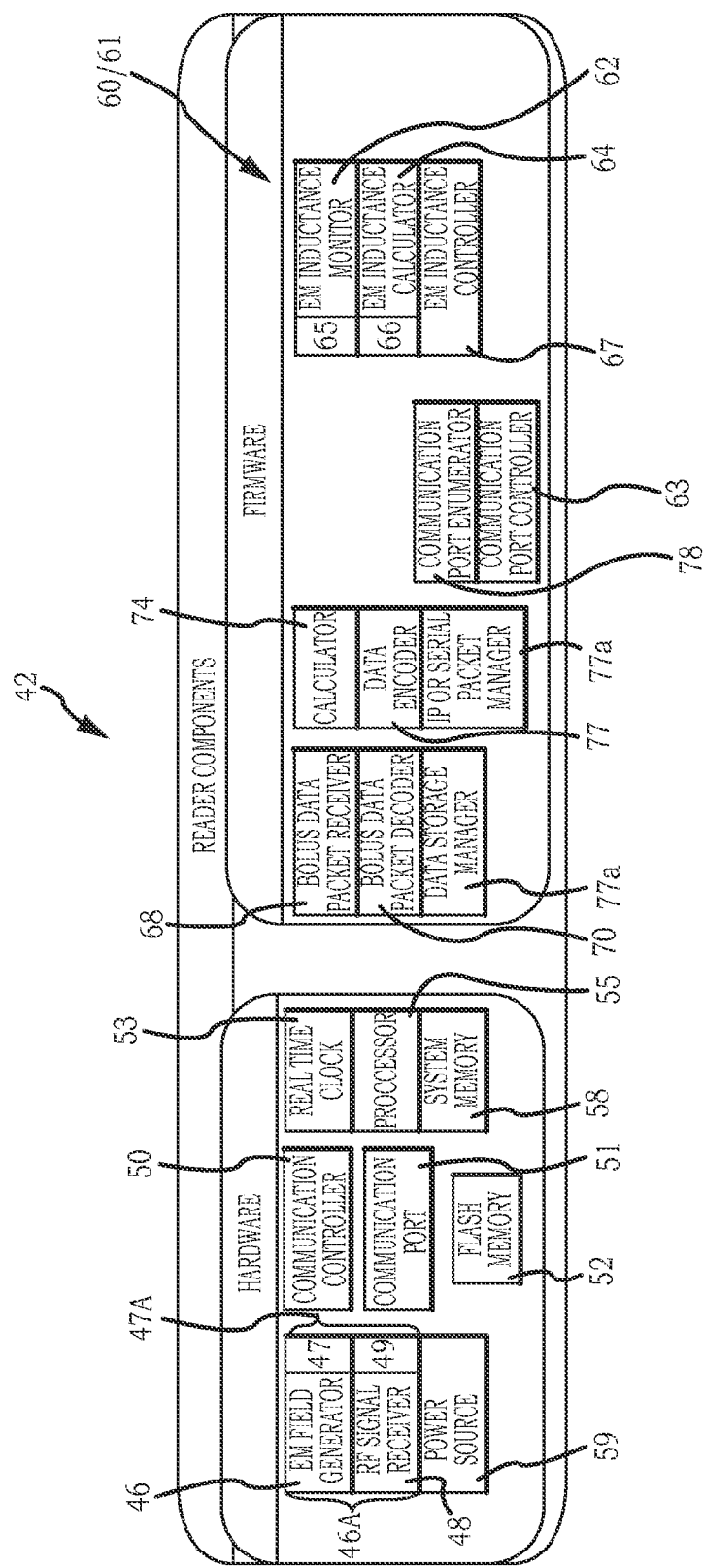
FIG. 2 is a block diagram of a RFID reader having hardware and firmware of a particular embodiment of the invention.

Now referring primarily to FIGS. 1 and 2, the computer implemented animal management system (or RFID object management system) can further include an RFID reader (42) (or plurality of RFID readers). The RFID reader(s) (42) may transmit a radio-frequency carrier signal (43) to the RFID (19). The RFID (19) may respond to the radio-frequency carrier signal (43) with a RFID data signal (44) to send and receive an amount of RFID information (45) from the RFID (19), or the like.

One non-limiting embodiment of the RFID reader (42) shown in FIGS. 1 and 2, can provide hardware in the form of an electromagnetic field generator (46) which manages the power level and induction of an electromagnetic drive antenna (47) having inductance between about 3.5 H and about 4.5 H with a 1 to 4 twist, a radio frequency signal receiver (48) which manages a receiving antenna (49) which collects the amount of RFID information (45) sent by the RFID (19) (as one example Digikey Part No. TH71111ENE-ND). In another non-limiting embodiment, a radiofrequency module (46a) (as one non-limiting example a RF Monolithics, Inc., Part No. TR7000) which manages a single antenna (47a) (as a non-limiting example a Linx Technologies Part No. ANT-433-MHW-SMA-S) for both sending and receiving of RFID information (45).

The RFID reader (42) hardware, can further include a RFID reader processor (55) which can perform computations based on sensed RFID object information (56) (which can be sensed animal information where the RFID object is an animal (40)) (see for example FIG. 3) and calibration data (57) (see for example FIG. 3) (as non-limiting examples Intel Part No. T80960SA16; Digikey Part No. 803846-ND). A first RFID reader memory (52) can store the amount of RFID information (45) transmitted with the radio-frequency carrier signal (43) (as non-limiting examples Intel Part No. GT28F160B3BA9DSB93, Digikey Part No. CAT28F512LI-12-ND). In an alternative the RFID reader processor (55) can integrally include the first RFID reader memory (52) (as non-limiting examples, Intel Part No. TN80960SA16; Digikey Part No. 8093846-ND; or Microchip Technology Part No. 2411256-I/SM EEPROM). A second RFID reader memory (58) used by the RFID reader processor (55) can perform read-write functions (as one non-limiting example Digikey Part No. CAT1640WI-42-T3cT-ND).

The hardware can further include a communication controller (50) which provides communication with the server computer (1) or remote computer (34) via LAN or WAN (as non-limiting examples Intel Part No. DA82562EM; Digikey Part No. 829707-ND); a LAN port or a WAN port (51) for wired or wireless connection to the server computer (1) or remote computer (34) (as non-limiting examples of wired port connection Amphenol Part No. RJHSE-5381; Digikey Part No. 829707-ND or wireless port connection specification 802.11 revs. a, b, g, or n or bluetooth rev. 1 or bluetooth rev. 2). In alternate embodiment the RFID reader processor (55) can be programmed to further provide the functionalities of the communication controller (50) in the form of Intel Part No. TN80960SA16; Digikey Part No. 8093846-ND; or Microchip Technology Part No. 2411256-I/SM EEPROM.

A clock (53) (as non-limiting examples Digikey Part No. CAT24C256WI-G-ND; Digikey Part No. MC88LV926DWR2T-ND; or NPX Semiconductor Part No. PCF8583TD-T) can function to govern timing of events controlled by the RFID reader processor (55) and couples a date-time stamp (54) (see FIG. 3) to the amount of RFID information (45).

A RFID reader power source (59) (typically 12 volt direct current in the range of 3.5-4.5 amperes) which can include a voltage regulator (as a non-limiting example a Digikey Part No. LM317D2TR4GSCT-ND).

Again referring primarily to FIGS. 1 and 2, the particular embodiment of the RFID reader (42) shown can further include a RFID reader application (60) (see "firmware" in FIG. 2) in the form of RFID reader modules (61) which can be stored in the first RFID memory (52) of the RFID reader (42) (or could be located in the computer server (1) or in the remote computer (34), as shown in FIG. 1). The RFID reader modules (61) stored and implemented by the hardware above-described can include an electromagnetic induction monitor module (62) which functions to monitor current inductance levels (65) in the electromagnetic drive antenna (47), an electromagnetic inductance calculator module (64) which functions to compare current electromagnetic inductance levels (65) to a target electromagnetic inductance level (66), and an electromagnetic inductance controller (67) which functions to adjust current electromagnetic inductance level (65) toward the target electromagnetic inductance level (66).

Figure 3:
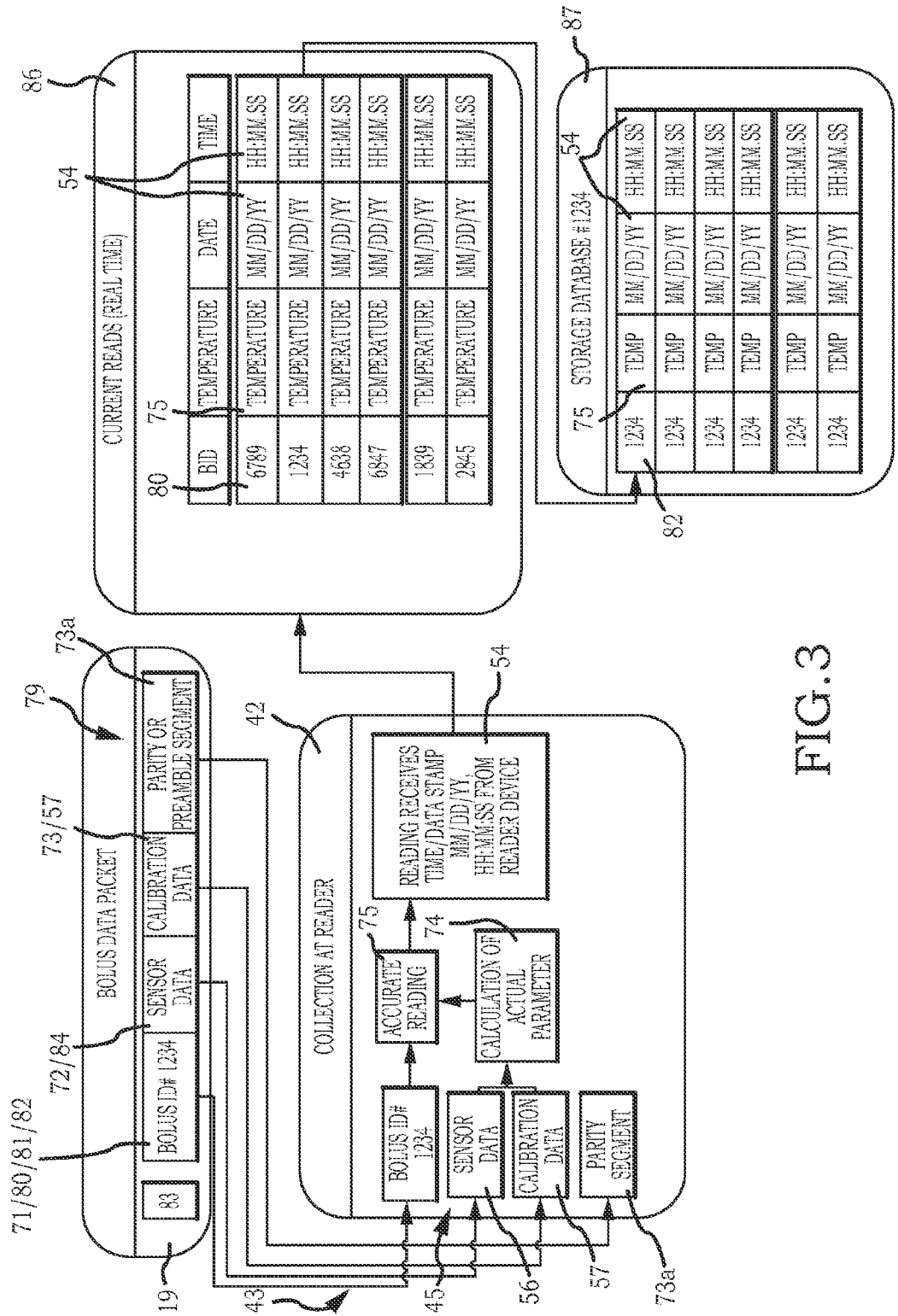
FIG. 3 is a block diagram which shows a particular embodiment of the invention which includes a bolus containing at least one sensor which provides sensed RFID object information and an RFID to which sensed RFID object information can be encoded and subsequently collected by an RFID reader.

Again referring primarily to FIGS. 2 and 3, the particular embodiment of the RFID reader (42) shown can further include RFID reader modules (61) located in the first RFID memory (52) of the RFID reader (42) including a receiver module (68) which functions to create a execution handle to receive the RFID data signal (44) transmitted with the radio-frequency carrier signal (43) from the RFID (19). The receiver module (68) can be activated by detection of movement of an RFID object (39) in the electromagnetic field (69) generated by the electromagnetic field generator (46). The receiver module (68) transfers the RFID data signal (44) which can be decoded by a decoder module (70). The decoder module (70) can be activated by the receiver module (68) and can further function to separate RFID information (45) from a plurality of bit segments (71)(72)(73) of the RFID (19) (see for example FIG. 3 and as further described below). The decoder module (70) can as to certain RFID information (45) activate a RFID reader calculator module (74) (see FIG. 3) to perform calculation functions and generate RFID object characteristic values (75) from sensed RFID object information (56) (see FIG. 3). A data management module (76) which can function in part to activate an RFID data encoder module (77) which functions to assemble transmitted RFID information (45) of the bit segments (71)(72)(73) of the RFID (19) (see FIG. 3) into a form which can be used by the data management module (76). A serial packet manager (77a) handles data packets output from the RFID reader data encoder module (77) to the communication port (51) for LAN or WAN transmission. A communication port enumerator module (78) functions to assign communication port information for a port controller module (63) which functions to control communications between the data management module (76) and server computer (1) or the remote computer (34).

While the above example describes the components of a RFID reader (42) (including hardware implements the functionalities of the firmware) which can be used with the inventive computer implemented animal management system; the invention is not so limited and a numerous and wide variety of RFID readers (42) known to those of ordinary skill in the art can be made compatible with the functionalities of the animal tracking application (17) further described herein, as one non-limiting example, hand held scanners available from Symbol Technologies, Inc., One Symbol Plaza, Holtsville, N.Y. 11742 and RFID tags from Alien Technology, 1830 NDSU Research Circle North, Forgo, N. Dak. 58103.

Now referring primarily to FIGS. 1 and 3, as to certain embodiments of the computer implemented animal management system, the RFID (19) can be located in the hollow inside of a bolus (79). Certain configurations of the bolus (79) can be ingested by certain RFID objects (39), such as cattle and be retained in a part of the stomach; although the invention is not so limited. A first bit segment (71) of the RFID device (19) implanted in an animal (40) can be encoded or re-encoded with an amount of RFID object identification information (80) (which can be a bolus identification number (81), animal identification number (82), or the like). A second bit segment (72) of the RFID (19) can be encoded or re-encoded from time to time with sensed RFID object characteristics (84) received from a sensor (83) which can be located within the bolus (79) or otherwise implanted within the RFID object (39) whether an animal (40) or an asset (41). For the purposes of this invention, sensed RFID object characteristics (84) can include without limitation a sensed characteristic of the RFID object (39), animal (40) or asset (41), for example, any one or more of location, temperature, pH, or the like, or any one or more of physiological characteristics of an animal (40) such as temperature, pH, heart rate, blood pressure, partial pressures of dissolved gases, or the like. The sensor (83) can as non-limiting examples be an omnidirectional tilt and vibration Sensor (PN SQ-SEN-200) distributed by Signal Quest Precision Microsensors; a Betachip Thermistor (PN 1K2OG3) distributed by BetaTHERM Sensors; a humidity sensor (PN HCZ-D5) distributed by Ghitron Technology CO., Ltd; an ultra miniature pressure transducer (PN COQ-062) distributed by Kulite, a proximity sensor (PN PY3-AN-3) distributed by Automation Direct.com. Variation of the sensed RFID object characteristic(s) (84) can be continuously or intermittently updated by encoding or re-encoding the second bit segment (72) of the RFID (19). A third bit segment (73) of the RFID (19) can be encoded or re-encoded from time to time with an amount of calibration data (57) which allows a RFID object characteristic value (75) to be calculated from the sensed RFID object characteristic (84) of the RFID object (39), animal (40) or asset (41).

The RFID object identification information (80), the sensed RFID object characteristics (84), and the amount of calibration data (57) can be collected from the corresponding first bit segment (71), second bit segment (72), and third bit segment (73) of the RFID (19) by the RFID reader (42), as above described, when the RFID object (39) passes within sufficiently close proximity of the RFID reader (42). As to certain embodiments of the RFID reader (42) the RFID object identification information (80) and the sensed RFID object characteristics (84) and the calibration data (57) can be received by the RFID reader (42) and coupled to a time-date stamp (54) (which for example can take the form of HH:MM:SS and MM/DD/YY). The RFID object characteristic value

(75) can be calculated by operation of a RFID reader calculator module (74) having a location in the RFID reader (42) or in the server computer (2) or the remote computer (34) (as to certain embodiments) using the sensed RFID object characteristic (74) and the calibration data (57). A parity segment (73a) can be located at the beginning and the end of the RFID information (45) from a plurality of bit segments (71)(72)(73) to identify the start and the stop of the RFID information (45).

The RFID object identification information (80) and the sensed RFID object characteristics value (75) can be separated, sorted and loaded into a current reads database table (86) stored in the first RFID memory (52) or in the server computer (1) or in the remote computer (34) memory (as to certain embodiments). The current reads database table (86) matches the calculated RFID object characteristic value (75) and time-date stamp (54). The calculated RFID object characteristic value (75) and time-date stamp (54) matched to the RFID object identification information (80) in the current reads database table (86) can in a further step be separated or sorted by RFID object identification information (80)(or a bolus identification number (81) animal identification number (82) for animal (40) embodiments) and the current reads for each of a plurality of individual RFID objects (39) can be stored in a corresponding plurality of RFID database tables (87) stored in a memory element (3) of the server computer (1) or remote computer (34) for retrieval by RFID object identification information (80) (animal identification number (82) or bolus identification number (81) depending upon the application of the invention).

Again referring primarily to FIG. 3, which provides a non-limiting example of a RFID object database table (87) ("Storage Database #1234 in the example) which includes the current reads for the RFID object (39) (#1234) in which the sensed RFID object characteristic (84) of the RFID object (39) is temperature calculated by operation of the a RFID reader calculator module (74) utilizing sensed RFID object characteristic (84) (temperature) and calibration data (57) to produce a RFID object characteristic value (75) representing the temperature of the RFID object (39) which can be for example the temperature of a bovine animal which can be encoded by or assembled or matched with the animal identification number (82) (or bolus identification number (82)) and the date-time stamp (54) into the RFID object database table (87) by the a data encoder module (77) or encoder-decoder application (18) at the level of the server computer (1) or remote computer (34).

Figure 4:
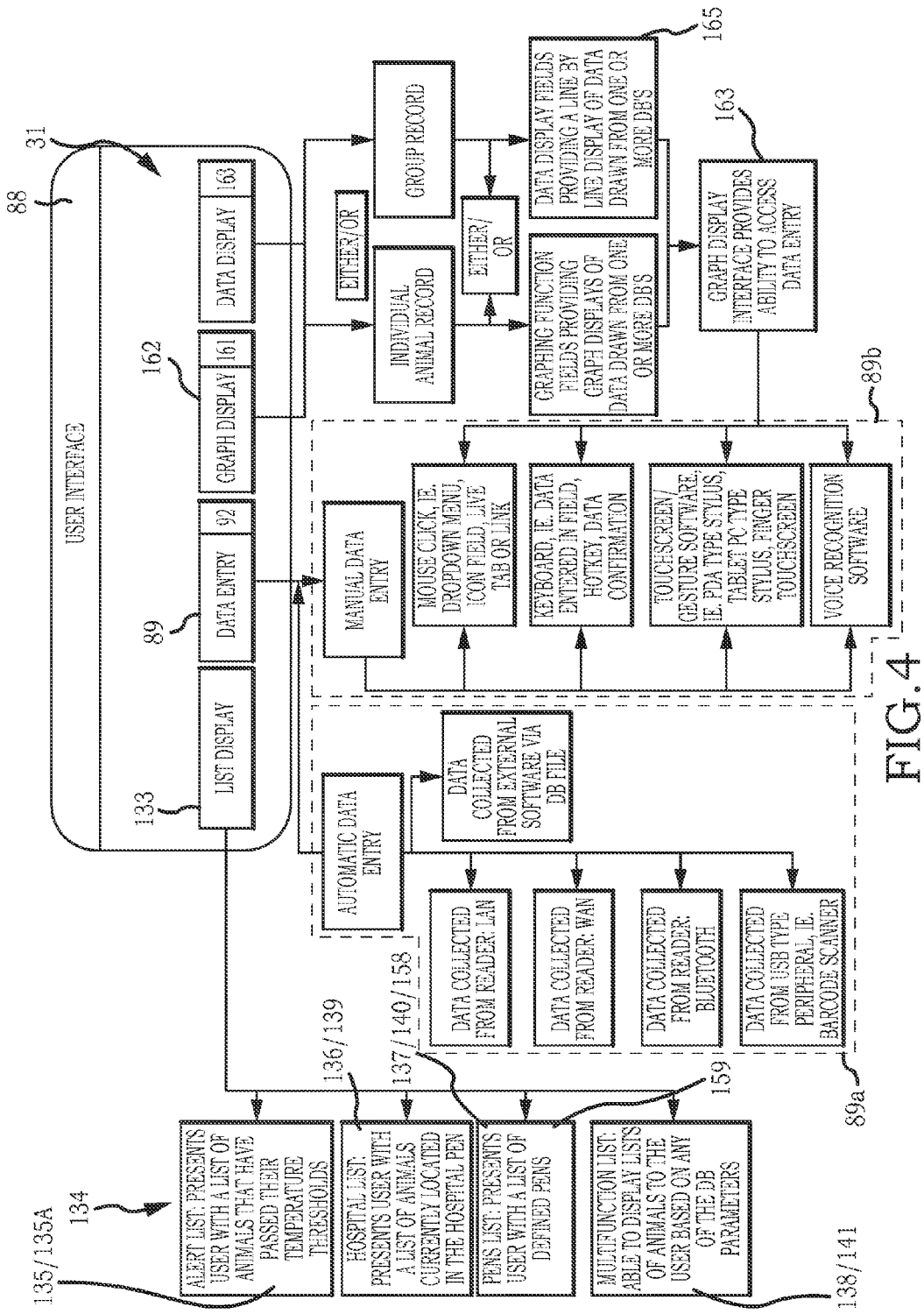
FIG. 4 is block diagram of a particular embodiment graphic user interface which can be generated by a particular embodiment of the animal management application of the invention.

RFID object characteristic values (75), the date-time stamp (54), and the animal identification number (82) encoded or assembled can be automatically entered into the current reads database table (86) and automatically separated by animal identification number (82) and automatically entered into the RFID object database table (87) data can be transmitted from the RFID reader (42) in a LAN or WAN or BLUETOOTH environment or collected from a USB peripheral such as a barcode scanner, or collected from a external database (see FIG. 4 "Automatic Data Entry" (89a)) to the server computer (1) or the remote computer (34).

Figure 5:
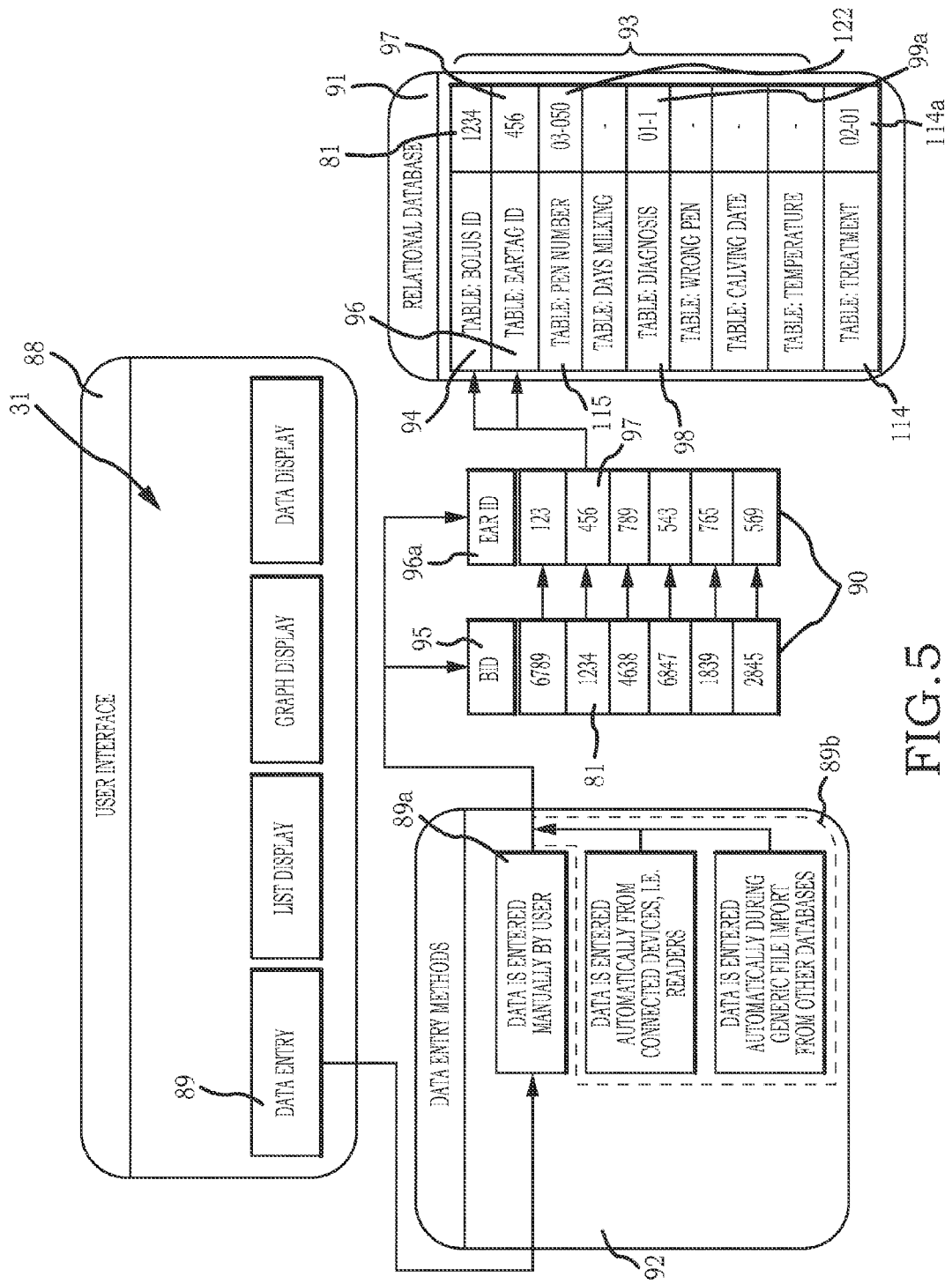
FIG. 5 is block diagram which shows the functionalities of a particular embodiment of a manual data entry module of the animal management application of the invention in regard to entry of RFID identification information into RFID object relational databases.

Again referring primarily to FIGS. 4 and 5, the animal management application (17) of the server computer (1) can further function to generate a graphic user interface (88) which can be viewed on the monitor (26) of the server computer (1) the remote computer (34) and provides control icons (31) (or fields or other interactive indicia) which by click event activate certain modules of the animal management application (17). In one non-limiting embodiment of the animal management application (17), the generated graphic user interface (88) provides a data entry icon (89) which upon click event generates data entry tables (90) (see for example FIG. 5) into which data can be automatically entered (89a) or manually entered (89b) (see FIG. 4 "Manual Data Entry") for transfer to RFID relational database tables (91) and RFID object database tables (87) by click event such as mouse click of drop down menus, key board, touch screen, PDA stylus, voice recognition, or the like, as further described below.

Now referring primarily to FIG. 5, click event on the data entry icon (89) activates a manual data entry module (92) which can function to generate a RFID object relational database table (91) which provides a list of relational tables (93) having linked relation to each other. While the particular examples provided by this description and the corresponding Figures may utilize particular terms to readily identify particular tables; however, these terms are not intended to be limiting with respect to the breadth of the functionality encompassed by that particular table. By click event, for example, on the Table: Bolus ID (94), a bolus identification table (95) or bolus identification field can be generated into which a bolus identification number (81) can be entered. Entry of the a bolus identification number (81) (for example 1234) into the bolus identification table (95) operates to change the bolus identification number (81) in the RFID object relational database table (91) assigned to the particular animal (40). Similarly, by click event on the Table: Ear tag ID (96) in the list of relational tables (93), an ear tag identification table (96a) can be generated into which an ear tag identifier (97) can be entered. Entry of the ear tag identifier (97) into the ear tag identification table (96a) operates to change the ear tag identifier (97) in the RFID object relational database table (91) assigned to the particular RFID object (39) (in this example an animal (40)).

Figure 6:
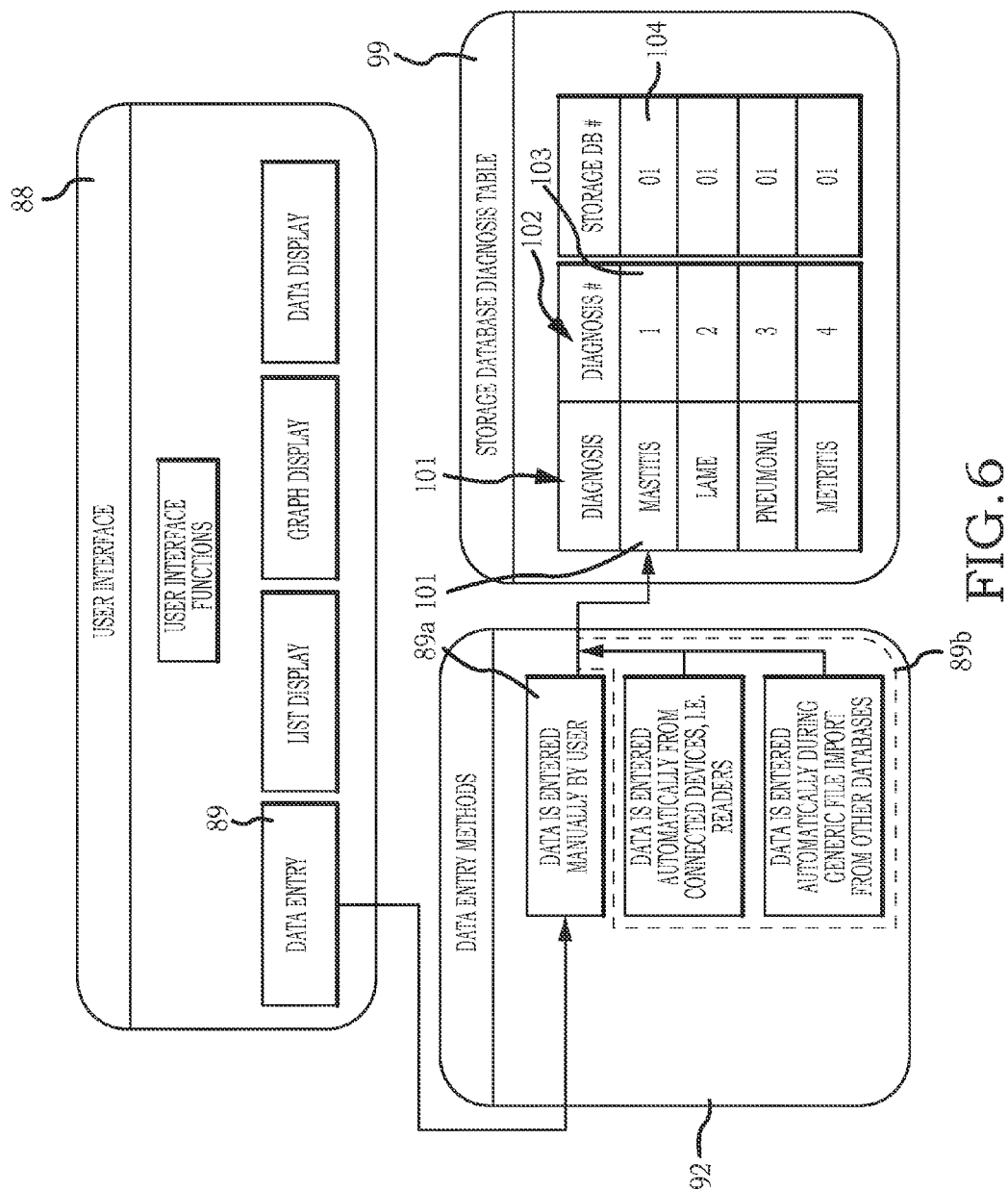
FIG. 6 is block diagram which shows further functionalities of a particular embodiment of a manual data entry module of the animal management application of the invention in regard to entry of diagnosis information into RFID storage database tables.

Now referring primarily to FIG. 6, click event on the data entry icon (89) can activate the manual data entry module (92) which can function to display a RFID object relational database table (91) which provides a list of relational tables (93) which have linked relation to each other. Click event in any one of the list of relational tables (93) (for example, on "Table: Diagnosis" (98)) (see for example FIG. 5) can generate a RFID object database table (91) (in this example the "Storage Database Diagnosis Table" (99)) (see FIG. 6) which can be configured to include any number of diagnosis identifiers (100) (for example row "Mastitis" (101)). Each diagnosis identifier (100) can be matched with a diagnosis identifier number (102) (Mastitis matched with diagnosis identifier number 1 (103)) and matched with a storage database identifier (104) (Mastitis matched with storage database 01). Upon entry of the diagnosis identifier (101) matched with the diagnosis identifier number (103) and storage database number (104) the animal management application (17) can function to update the RFID object relational database table (91) of the RFID object (39) (animal (40)) to include the diagnosis status (99a) in the correspondingly linked field (refer to FIG. 5 in which the linked field Table: Diagnosis has been updated to include 01, 1 for the RFID object relational database table (91) of the animal (40) associated with ear tag identifier (97) ("456").

Figure 7:
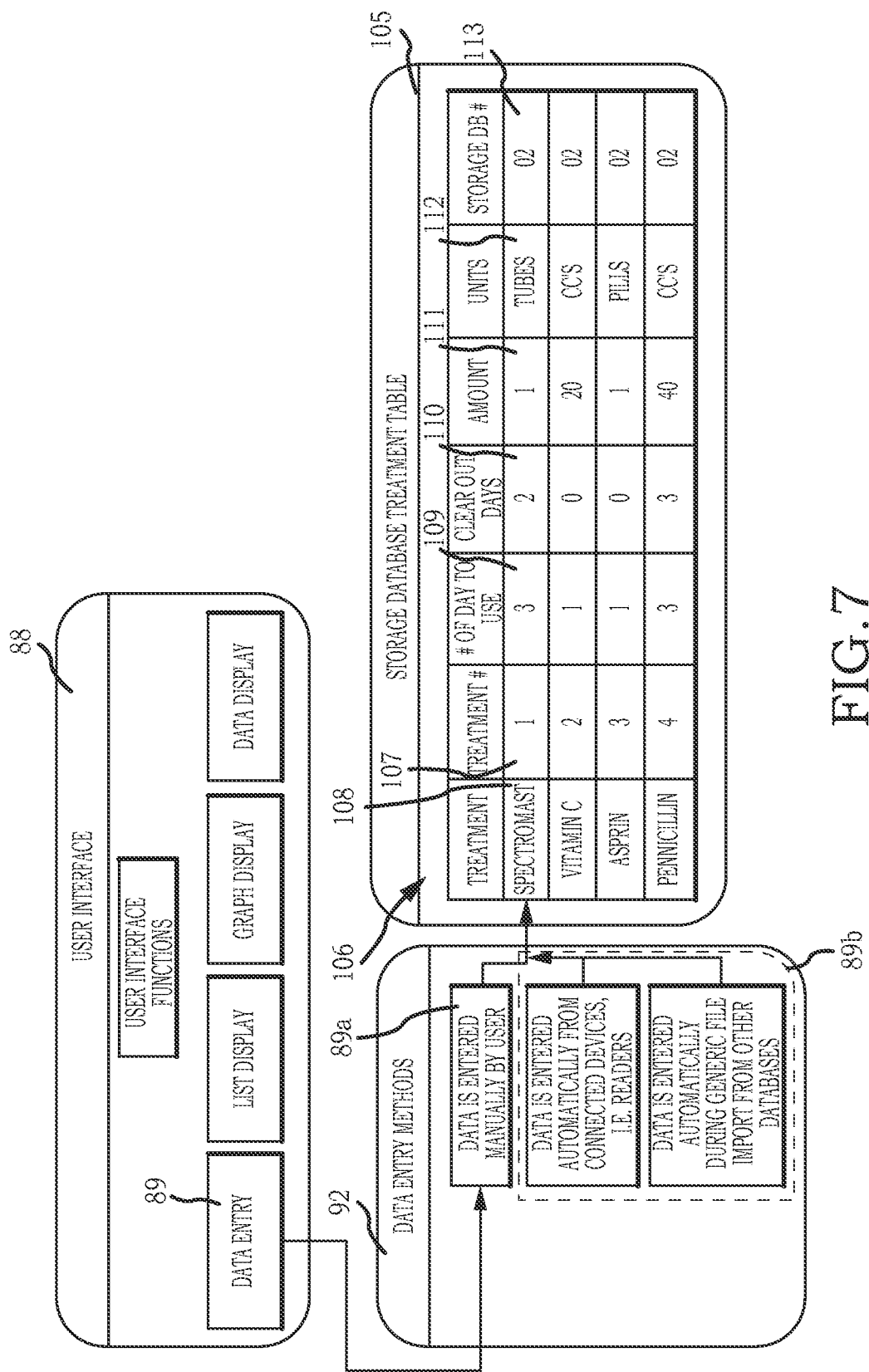
FIG. 7 is block diagram which shows further functionalities of a particular embodiment of a manual data entry module of the animal management application of the invention in regard to entry of treatment information RFID storage database tables.

Now referring primarily to FIG. 7, as one additional non-limiting example, click event on the data entry icon (89) can further activate the data entry module (92) to provide the RFID object storage database table (91) of a particular RFID object (39) (animal (40)). By click event on Table: Diagnosis (98), a Treatment Storage Database Table (105) can be graphically displayed which allows a treatment plan (106) to be entered for a particular animal (40) including a treatment identifier (107) (typically a numeric value), the treatment material (108) (drug or other therapeutic material), the number of days of use (109), the number of clearance days (110), the number of units of treatment material (111), the units (112), and the storage database identifier (113). Upon entry of the treatment plan (106), the RFID object relational database table (91) of the particular RFID object (39) (animal (40)) (see FIG. 5) would be updated for example in the Table: Treatment (114) to include treatment status 02, 1 (114a) (see FIG. 5) identifying the treatment plan (106) for the RFID object (39) (animal (40)) having the related ear tag identifier (97) (bolus number (81)).

Figure 8:
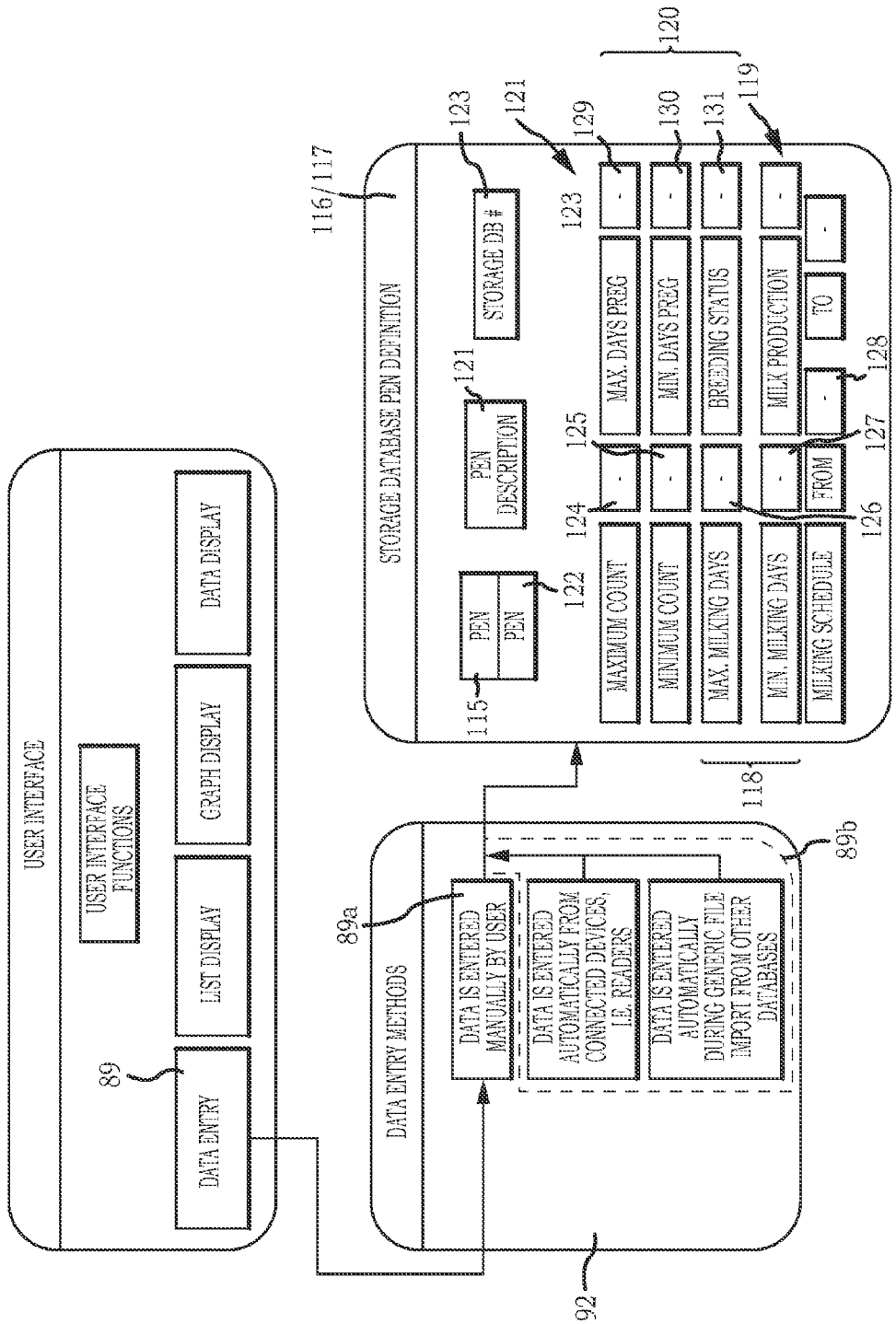
FIG. 8 is block diagram which shows further functionalities of a particular embodiment of a manual data entry module of the animal management application of the invention in regard to entry of pen definitions RFID storage database tables.

Now referring primarily to FIG. 8, as one additional non-limiting example, click event on the data entry icon (89) can further activate the data entry module (92) to retrieve the RFID object relational database table (91) of a particular RFID object (39) (animal (40). By click event in the RFID object relational database table (91) of "Pen Number" (115), a Pen Definition Storage Database Table (116) can be graphically displayed which allows a pen definition (117) to be created whether for a pen in general or for a pen in which to locate a particular the RFID object (39) (animal (40)). By creating a pen definition (117) for a RFID object(s) (39) (animal (40)), those RFID objects (39) (animals (40)) having a similar status such as days in milk (118), milk production (119), reproductive status (120), or the like can be grouped together in the same pen number(s) (115). Accordingly, the pen definition (117) can be created by selection or entry of pen definition elements (121) sufficient to define the pen for a category of RFID objects (39) (animal (40)) such as a pen description (121) (such as high production, low production, or the like), pen number (122), RFID object database table identifier (123), maximum count (124), minimum count (125), maximum milking days (126), minimum milking days (127), milking schedule (128), maximum days pregnant (129), minimum days pregnant (130), breeding status (131), milk production (132), or the like. Upon entry of the pen definition elements (121) the pen number (122) and the RFID object database table identifier (123) can be updated into the RFID object relational database tables (91) (see FIG. 5 showing pen status identifier (115a) as 03-050).

Again referring primarily to FIG. 4, the animal management application (17) of the server computer (1) can further function as above described to generate the graphic user interface (88) which further provides control icons (31) which by click event activate provides a list display icon (133) which upon click event displays a plurality of list icons (134) such as an Alert List (135), a Hospital List (136), a Pens List (137), or Malfunction List (138) each of which upon click event activates the functionalities of a corresponding alert module (135a), hospital module (139), pen module (140), or malfunction module (141), or the like, as further described below.

Figure 9:
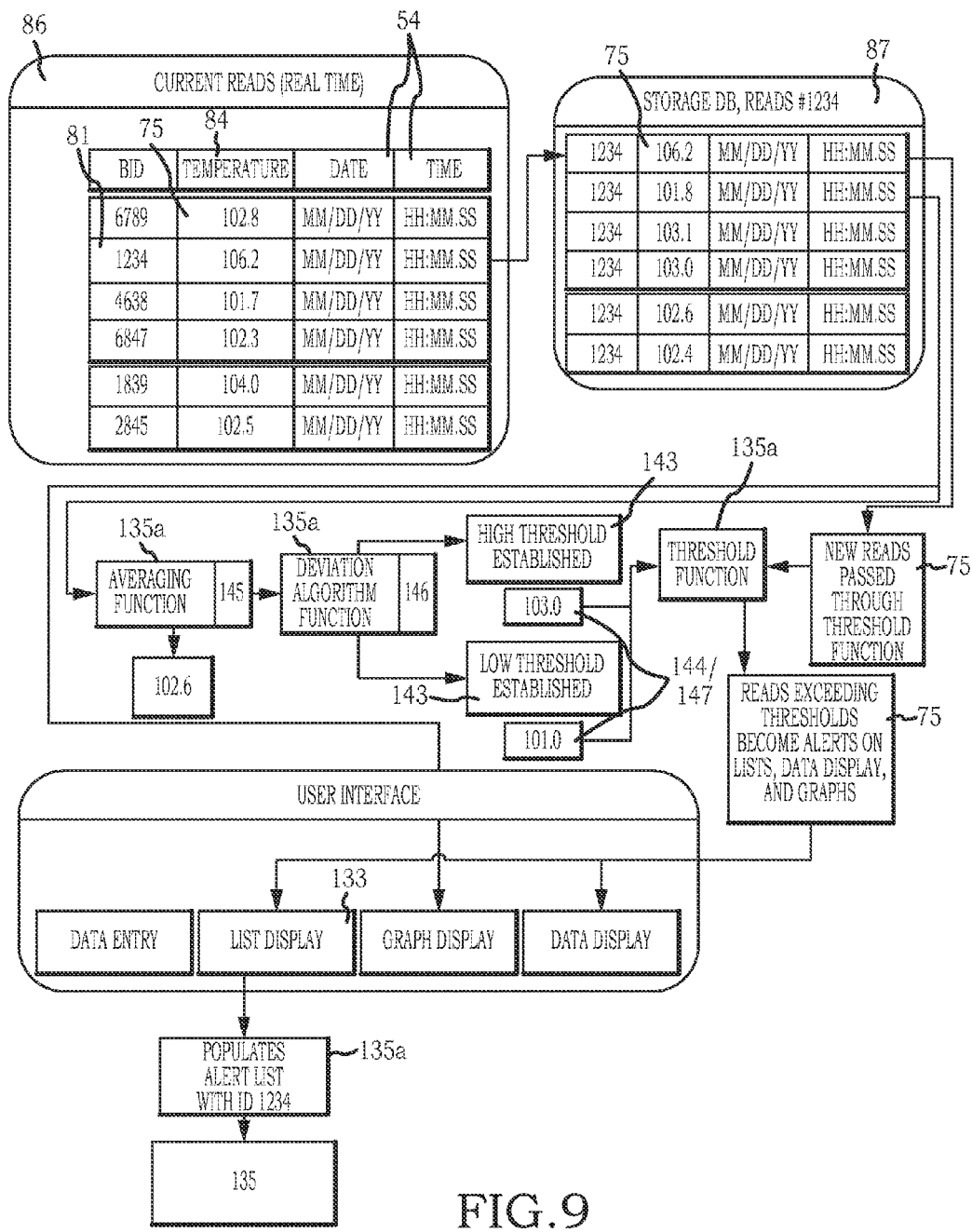
FIG. 9 is block diagram which shows the functionalities of a particular embodiment of an alert module of the animal management application of the invention in regard to generating an alert list relating to RFID objects having sensed RFID object characteristics which exceed threshold limits for a particular RFID object characteristic.

Now referring primarily to FIG. 9, which provides a block diagram which illustrates how the alert module (135a) populates an alert list (135). While the example provided by FIG. 9, illustrates how the alert module (135a) operates for the sensed RFID object characteristic (84) of sensing temperature of an animal (40); the invention is not so limited and any sensed RFID object characteristic (84) for which a RFID object characteristic value (85) can be generated and compared to a corresponding threshold range (143) can be the basis for populating an alert list (135) for the sensed RFID object characteristics (84) such as location, temperature, pH, heart rate, blood pressure, partial pressures of dissolved gases, or the like, in accordance with the invention.

Now referring primarily to FIGS. 3 and 9, which provides a non-limiting example of a sensed RFID object characteristic (84) which can be updated from time to time as an RFID object characteristic value (75) for temperature in the current reads database table (86) and the RFID object database table (87) and stored in the memory element (3) of the server computer (1) or remote computer (34), as above described. The alert module (135a) can further function to compare the updated RFID object characteristic value (75) for a particular RFID object (39) (animal (40) in this non-limiting example the sensed temperature of bolus identification number (81) 1234 (BID#1234)) with the prior established threshold values (144) (for example a high threshold value and a low threshold value for BID#1234) for the sensed RFID object characteristic value (75) for temperature of the same animal (40) (see for example FIG. 9). As to certain embodiments, the alert module (135a) can function to average all the prior sensed RFID object characteristic values (75) for a particular sensed RFID object characteristic (84) (in the instant example temperature values for BID#1234) of a particular RFID object (39) (animal (40)) to generate a mean value (145) for the prior sensed RFID object characteristic values (75) for temperature (for example as shown in FIG. 9 a mean temperature of 102.6° F. fpr BID#1234). The alert module (135a) can further operate on all of the prior sensed RFID object characteristic values (75) for temperature of that particular RFID object (39) (animal (40) BID#1234) to establish a mean deviation value (146). The alert module can utilize the mean deviation value (146) to generate a RFID object characteristic value range (147) for the sensed RFID object characteristic values (75) (temperature) for that particular RFID object (39) (animal (40) BID#1234 as shown FIG. 9 a range (147) of about 103° F. to about 101.0° F.). The numeric value at the either end of the RFID object characteristic value range (147) provides the threshold values (144) against which sensed RFID object characteristic values (temperature values for BID#1234 in the instant example) can be compared by function of the alert module (135a). The alert module (135a) can then compare each new sensed RFID object characteristic value (75) to the threshold values (144). The alert module (138) can then function to populate the alert list (135) (viewable by click event on the list display icon (133)) with RFID object identification information (80) (such as BID#1234) coupled to RFID object characteristic values (75) (in the instant example temperature values) which are outside of the value range (147) established by the threshold values (144).

Figure 10:
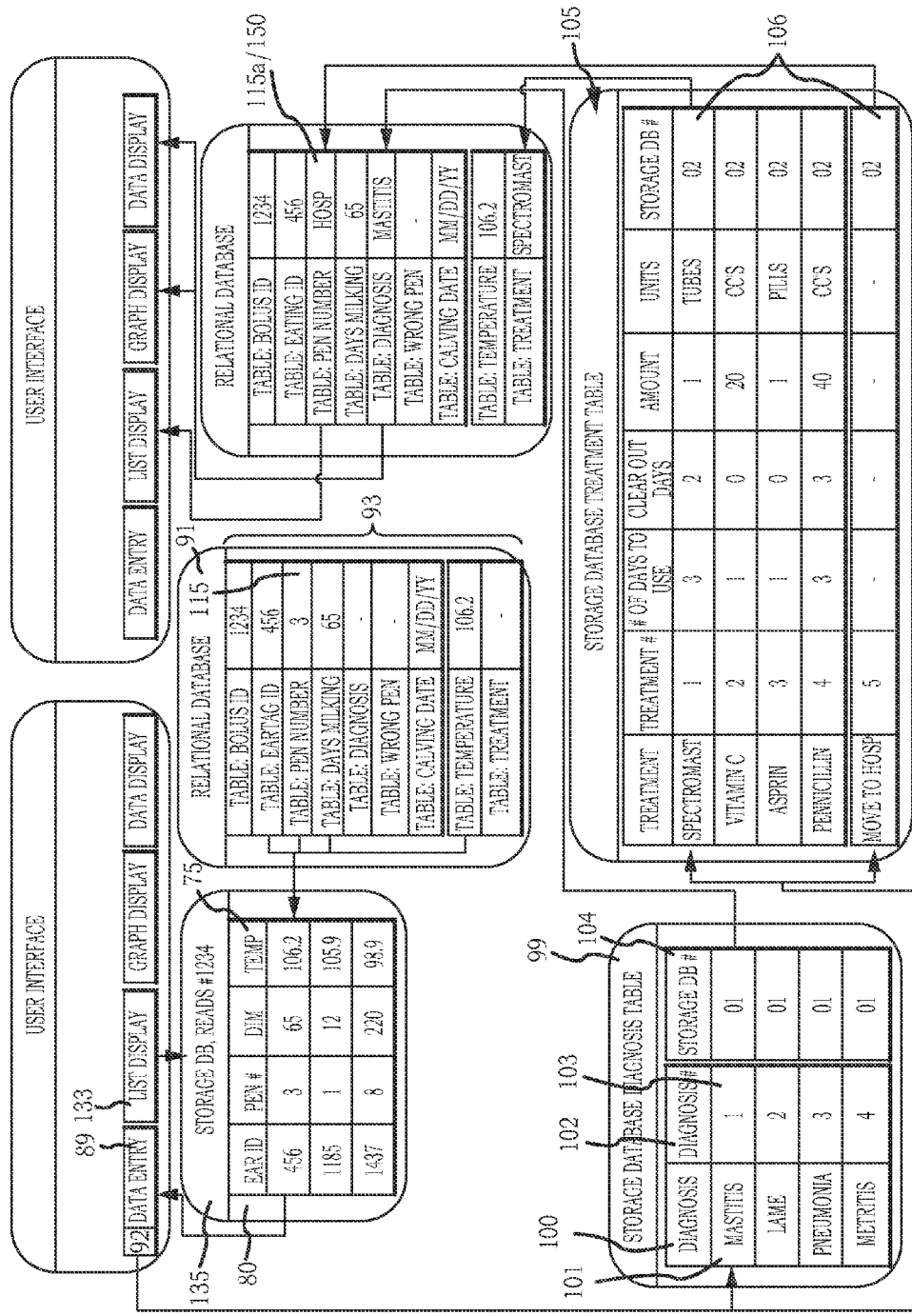
FIG. 10 is block diagram which shows the functionalities of a particular embodiment of an alert module of the animal management application of the invention in regard to generating an alert list relating to RFID objects having sensed RFID object characteristics which exceed threshold limits for a particular RFID object characteristic.

Now referring primarily to FIG. 10, which shows an alert list (135) populated with RFID object identification information (80) having a sensed RFID object characteristic value (75) (in the instant example, temperature values of animal (40)) that fall outside of the RFID object characteristic value range (147) thresholds (144)). The alert list module (135a) can further function upon click event of a listed RFID object (39) (or the object identification information (80) and in this example again referring to BID#1234) to retrieve the corresponding RFID object relational data base table (91) for the listed RFID object (39) (animal (40)), as above described. The RFID object relational data base table (91) allows the RFID object (39) (animal (40)) to be located by pen number (115) (in the example BID#1234 located in Pen Number 3). As further shown in FIG. 10, and as prior described, by click event in the list of relational tables (93) the manual data entry module (92) can function to allow entry of diagnosis identifiers (100) and a treatment plan (106), as described above, into the Diagnosis Table (99) and Treatment Table (105). The RFID object relational database table (91) of the particular RFID object (39) (animal (40)) (see FIG. 5) can be updated to include the new Pen Number (115a) (Hospital Pen 150) and treatment status 02, 1 (114a) (see for example FIG. 5) identifying the treatment plan (106) for the RFID object (39) (animal (40)) having the related ear tag identifier (97) (bolus number (81)).

Figure 11:
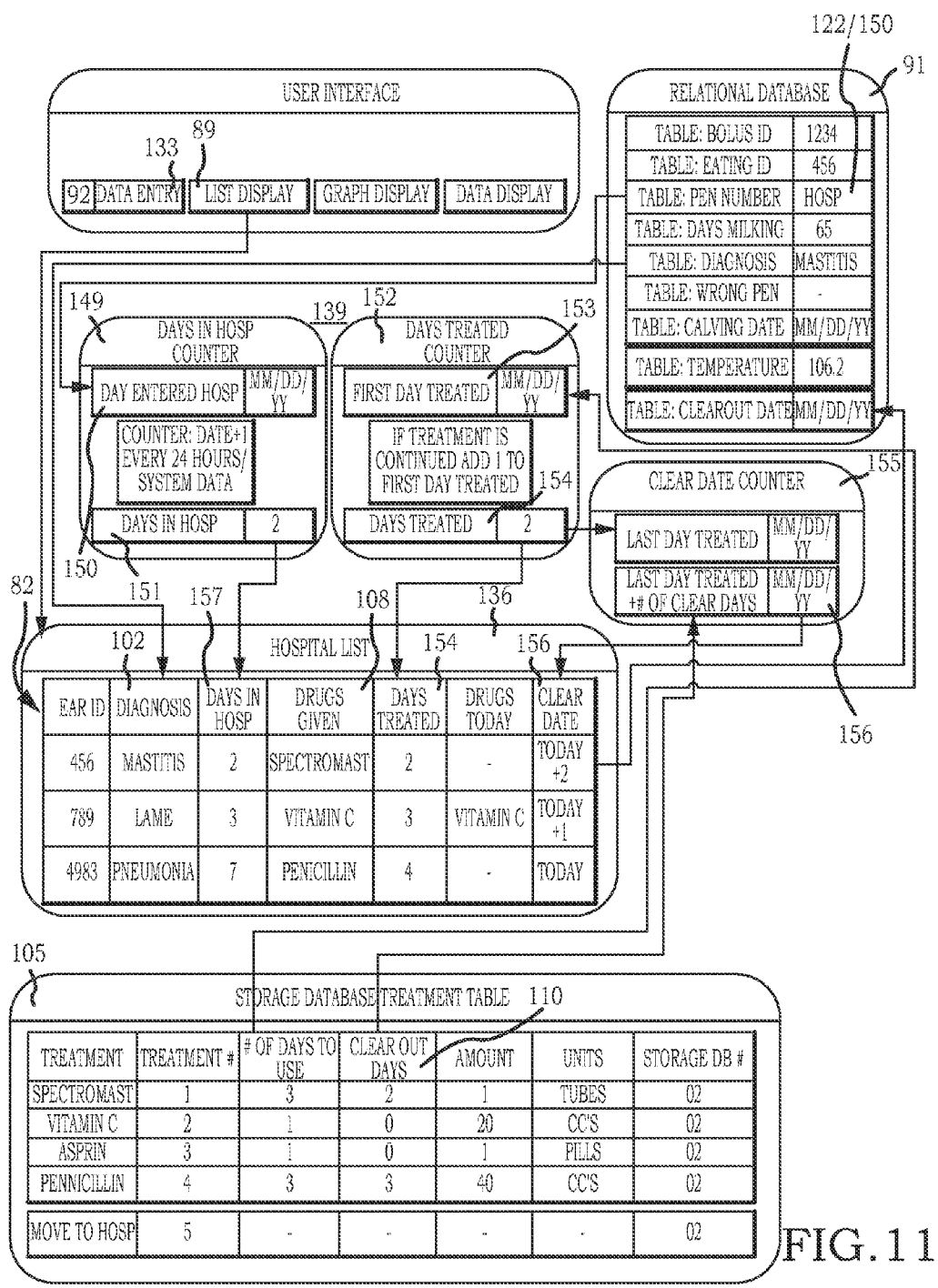
FIG. 11 is block diagram which shows the functionalities of a particular embodiment of a hospital module of the animal management application of the invention in regard to generating a hospital list of RFID objects which are receiving treatment in accordance with a treatment plan.

Now referring primarily to FIG. 11, which provides a block diagram which illustrates how the hospital module (139) populates a hospital list (136). The hospital module (139) includes a hospital days counter (149) which functions to count the number days (151) a particular RFID object (39) (animal (40)) has been located in a hospital pen (115b). The hospital days counter (149) retrieves from the corresponding RFID object relational data base table (91) and corresponding RFID object data base tables (87) the date time stamp (54) for the first day the RFID object (39) (animal (40)) was located in a hospital pen (150) and adds one day to a hospital day count (151) for each 24 hour interval the RFID object (39) remains in the hospital pen (150). The hospital module (139) further includes a treatment days counter (152) which retrieves the date time stamp (54) for the first day of treatment (153) of the RFID object (39) and adds one day to a treatment day count (154) for each treatment day of the RFID object (39). The hospital module (136) further includes a clearance date counter (155) which retrieves the treatment day count (154) from the treatment days counter (152) and the clearance out days (110) from the treatment storage database table (105) to calculate the treatment clearance date (156). The hospital module (136) can further function to draw upon the various RFID object data base tables (87) to generate a hospital list (136) and populate the hospital list (136) with animal identification number (82) in the hospital pen (150), diagnosis (102), hospital day count (157), treatment material (108), treatment day count (154), and clearance date (156).

Figure 12:
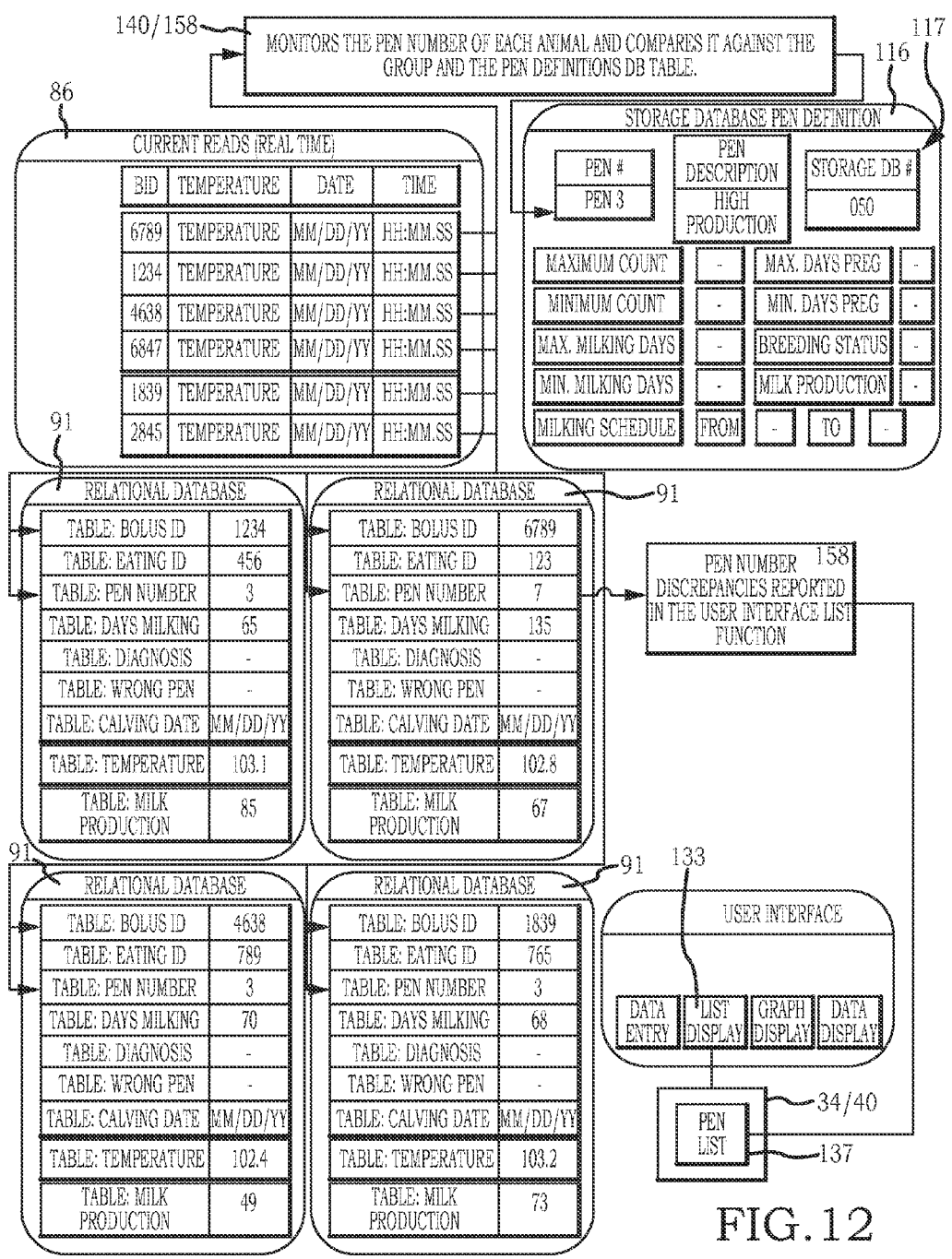
FIG. 12 is block diagram which shows the functionalities of a particular embodiment of a pen module of the animal management application of the invention relating to a watch module which functions to generate a list of RFID objects which are located in the incorrect location or pen number.

Now referring primarily to FIG. 12, which provides a block diagram that illustrates a functionality of a pen module (140) which populates a pen list (137) to show RFID objects (39) (animal (40)) which are not located in the correct pen number (122). In a first mode, the pen module (140) includes a pen watch module (158) which compares for each RFID object (39) (animal (40)) the pen definition (117) in the pen definition storage database (116) against the actual pen number (122) entered in the corresponding RFID object relational database table (91) for the RFID object (39) (40). The pen module (140) can further function to generate a pen list (137) of the RFID objects (39) having an actual pen number (122) which differs from the corresponding pen definition (117) in the pen definition storage database (116).

Figure 13:
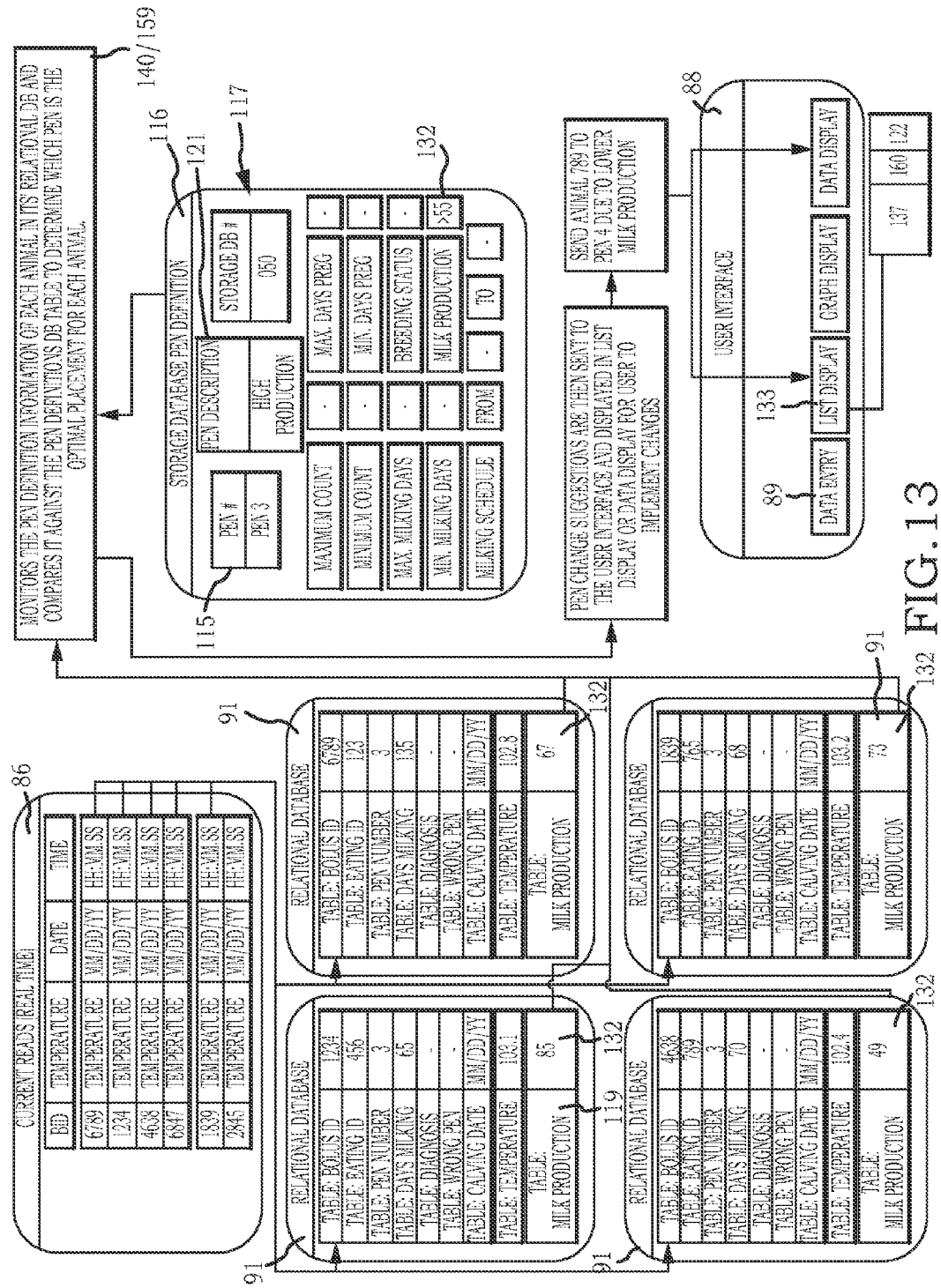
FIG. 13 is block diagram which shows the functionalities of a particular embodiment of a pen module of the animal management application of the invention relating to an autosort module which automatically sorts RFID objects into groups based on RFID object information and pen definitions such that animals of similar status can be grouped together.

Now referring primarily to FIG. 13, which provides a block diagram that illustrates another functionality of the pen module (140) which sorts RFID objects (39) based on comparison of the RFID information entered, as above described, into the data entry tables (90) of corresponding RFID object relational data base tables (91) of each RFID object (39)(40). As one non-limiting example, the pen description (121) (for example "high production") can correspond to an RFID object (39) (40) having milk production greater than a pre-selected milk production value (132) (for example ">55"). The sort module (159) can operate to compare the milk production value (132) listed for each of a plurality of RFID objects (39)(40) in the corresponding plurality of RFID object relational data base tables (91) to the pen description (121) for "high production". The sort module (159) can then operate to generate a pen list (137) of RFID objects (39)(40) with pen numbers (122) in which "high production" RFID objects can be optimally located. By click event in the graphic user interface (88) of the list display icon (133) and subsequent click event on pens list (133) and click event to activate the sort module (159) all the RFID objects (39) can be included in an sort list (160) with a corresponding optimal pen number (122).

Again referring to FIG. 4, the animal tracking system can further include a graph display module (161) which can function upon click event of a corresponding graph display icon (162) in the graphic user interface (88) to generate graphs (163) from data drawn from the RFID object relational data base tables (91) or the RFID object data base tables (87) of individual RFID objects (39)(40) or any particular grouping of RFID objects (39). Alternately, a data display module (163) can function upon click event of a corresponding data display icon (164) in the graphic user interface (88) to generate data display fields (165) which provide a line by line display of data drawn from one or more RFID object relational data base tables (91) or RFID object database tables (87).

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As to any particular value or any particular range the term "about" means within ten percent of the numerical value or numerical value of the end points of a range.

Moreover, for the purposes of the present invention, the term "a" or "an" entity refers to one or more of that entity; for example, "a relational data base table" refers to one or more of those relational data base tables. As such, the terms "a" or "an", "one or more" and "at least one" can be used interchangeably herein.

As can be easily understood from the foregoing, the basic concepts of the present invention may be embodied in a variety of ways which includes as one embodiment described the best mode of the invention. The invention involves numerous and varied embodiments of an animal tracking system. As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "server" should be understood to encompass disclosure of the act of "serving"—whether explicitly discussed or not—and, conversely, were there effectively disclosure of the act of "serving", such a disclosure should be understood to encompass disclosure of a "server" and even a "means for serving." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the computer implemented animal management systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A computer implemented method of animal tracking, comprising:
   connecting a computer to an RFID device reader;
   reading an RFID device implanted in an animal with said RFID device reader;
   retrieving an amount of animal identification information from said RFID device implanted in an animal;
   linking an amount of animal information of said animal stored in a data base of said computer to said amount of information retrieved from said RFID device implanted in said animal, said amount of animal information stored in said data base of said computer comprising an amount of milk production information or an amount of days milked;
   converting said amount of animal information of said animal stored in said database of said computer linked to said amount of information retrieved from said RFID device implanted in said animal into one or more logical variables;
   inserting at least one of said plurality of logical variables into at least one logical expression; and
   obtaining a logical value relating to said animal.

2. The computer implemented method of animal tracking as described in claim 1, wherein retrieving and linking comprise:
   retrieving an amount of animal identification information from a plurality of RFID devices implanted in a plurality of animals; and
   correspondingly linking an amount of animal information of said plurality of animals stored in said data base of said computer to said amount of information retrieved from said plurality of RFID device.

3. The computer implemented method of animal tracking as described in claim 2, further comprising retrieving an amount of date-time information from said plurality of RFID devices implanted in said plurality of animals.

4. The computer implemented method of animal tracking as described in claim 3, further comprising retrieving an amount of sensed animal information from said plurality of RFID devices implanted in said plurality of animals.

5. The computer implemented method of animal tracking as described in claim 4, further comprising retrieving an amount of animal location information from said plurality of RFID devices implanted in said plurality of animals.

6. The computer implemented method of animal tracking as described in claim 5, wherein retrieving an amount of sensed animal information from said plurality of RFID devices implanted in said plurality of animals further comprises retrieving an amount of sensed temperature information from said plurality of RFID devices implanted in said plurality of animals.

7. The computer implemented method of animal tracking as described in claim 6, wherein correspondingly linking an amount of animal information of said plurality of animals stored in said data base of said computer to said amount of information retrieved from said plurality of RFID device further comprises correspondingly linking an amount of health information corresponding to said plurality of animals stored in said data base of said computer to said amount of information retrieved from said plurality of RFID devices implanted in said animals.

8. The computer implemented method of animal tracking as described in claim 7, wherein retrieving an amount of animal location information further comprises retrieving an amount of animal pen location information from of said plurality of RFID devices implanted in said plurality of animals.

9. The computer implemented method of animal tracking as described in claim 8, wherein inserting at least one of said plurality of logical variables into at least one logical expression further comprises inserting an occurrence of illness for each of said plurality of animals in a selected pen during a selected period of time to determine whether there is a greater than selected number of said occurrence of illness.

10. The computer implemented method of animal tracking as described in claim 6, wherein correspondingly linking an amount of animal information of each of said plurality of animals stored in said database of said computer to said amount of information retrieved from said plurality of RFID devices implanted in said plurality of animals further comprises correspondingly linking an amount of desired pen count information to said amount of information retrieved from said plurality of RFID devices implanted in said plurality of animals.

11. The computer implemented method of animal tracking as described in claim 10, wherein inserting at least one of said plurality of logical variables into at least one logical expression further comprises inserting an amount of milk production information or an amount of days milked information.

12. The computer implemented method of animal tracking as described in claim 11, wherein obtaining a logical value relating to said animal comprises obtaining for a selected period of time for each of said plurality of animals which of a plurality of pens in which to locate each of said plurality of animals.

13. The computer implemented method of animal tracking as described in claim 6, wherein correspondingly linking an amount of animal information of said plurality of animals stored in said data base of said computer to said amount of information retrieved from said plurality of RFID device further comprises correspondingly linking an amount of date-time information as to administration of a first compound to each of said plurality of animals, an amount of date-time information as to administration of a second compound to each of said plurality of animals, an amount of date-time information as to occurrence of first compound effects on each of said plurality of animals, an amount of date-time information as to occurrence of second compound effects on each of said plurality of animals to said amount of information retrieved from said plurality of RFID devices implanted in said plurality of animals.

14. The computer implemented method of animal tracking as described in claim 13, further comprising inserting an amount of date-time information as to administration of a first compound to each of said plurality of animals, an amount of date-time information as to administration of a second compound to each of said plurality of animals, an amount of date-time information as to occurrence of first compound effects on each of said plurality of animals, an amount of date-time information as to occurrence of second compound effects on each of said plurality of animals.

15. The computer implemented method of animal tracking as described in claim 1, further comprising providing a server connected to said computer which provides a browser-based user interface which enables an animal tracker to track each of said plurality of animals based on said amount of information retrieved from each said bit segment of said plurality of RFID devices implanted in said plurality of animals.

16. The computer implemented method of animal tracking as described in claim 15, further comprising providing a computer network connected to said computer.

17. The computer implemented method of animal tracking as described in claim 16, further comprising providing a wide area network to which said computer connects.

18. The computer implemented method of animal tracking as described in claim 17, further comprising providing at least one client computer capable of configuration with said executable program instructions connected to said wide area network.

19. The computer implemented method of animal tracking as described in claim 18, wherein providing at least one client computer capable of configuration with said executable program instructions connected to said wide area network comprises providing a palm device capable of configuration with said executable program instructions connected to said wide area network.

20. The computer implemented method of animal tracking as described in claim 19, wherein providing at least one client computer capable of configuration with said executable program instructions connected to said wide area network comprises providing a cellular telephone capable of configuration with said executable program instructions connected to said wide area network.

21. The computer implemented method of animal tracking as described in any one of claim 18, 19, or 20, further comprising providing a portable RFID device reader.

22. The computer implemented method of animal tracking as described in claim 21, further comprising connecting said portable RFID device reader to said client computer.

23. The computer implemented animal tracking system as described in clam 21, further comprising connecting said portable RFID device reader to said wireless palm device.

24. The computer implemented animal tracking system as described in clam 21, further comprising connecting said portable RFID device reader to said cellular telephone.

25. The computer implemented animal tracking system as described in clam 21, wherein reading an RFID device implanted in an animal with said RFID device reader comprises reading an RFID device said RFID device part of a bolus ingested by a bovine animal.

* * * * *